(12) United States Patent
Chen et al.

(10) Patent No.: US 7,370,543 B2
(45) Date of Patent: May 13, 2008

(54) AIR-SAMPLING DEVICE AND METHOD OF USE

(75) Inventors: Teh-Hsun B. Chen, Morgantown, WV (US); Gregory Feather, Morgantown, WV (US); Jvoti Keswani, Morgantown, WV (US); Herbert David Edgell, III, Morgantown, WV (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/575,048

(22) PCT Filed: Oct. 1, 2004

(86) PCT No.: PCT/US2004/032378

§ 371 (c)(1),
(2), (4) Date: Apr. 4, 2006

(87) PCT Pub. No.: WO2005/040767

PCT Pub. Date: May 6, 2005

(65) Prior Publication Data

US 2007/0068223 A1   Mar. 29, 2007

Related U.S. Application Data

(60) Provisional application No. 60/512,252, filed on Oct. 17, 2003.

(51) Int. Cl.
*G01N 1/00* (2006.01)

(52) U.S. Cl. .................................................. 73/863.21

(58) Field of Classification Search ............... None
See application file for complete search history.

(56) References Cited

U.S. PATENT DOCUMENTS 4,178,794 A    12/1979   Jugle et al.

(Continued)

FOREIGN PATENT DOCUMENTS

HU           193716 B      11/1984

(Continued)

OTHER PUBLICATIONS

Definition of "microcentrifuge tubes", p. 3 of http://en.wickipedia.org/wicki/Laboratory_centrifuge.*

(Continued)

*Primary Examiner*—Robert Raevis
(74) *Attorney, Agent, or Firm*—Klarquist Sparkman, LLP

(57) ABSTRACT

The present disclosure concerns embodiments of a sampling apparatus that utilizes one or more cyclone separators to collect airborne particles from the atmosphere. In one representative embodiment, the sampling apparatus includes a collection-vessel retaining member that is adapted to be removably coupled to a collection vessel. The retaining member has an air-inlet conduit for permitting air to flow through the open end of the collection vessel and an air-outlet conduit for permitting air to exit the open end of the collection vessel. The airinlet conduit and the air-outlet conduit are configured to cause air flowing into the collection vessel to establishes a cyclonic flow path, which causes airborne particles to separate out from the air stream and collect in the collection vessel.

29 Claims, 10 Drawing Sheets

U.S. PATENT DOCUMENTS

| | | | |
|---|---|---|---|
| 4,292,574 | A | 9/1981 | Sipin et al. |
| 4,941,899 | A | 7/1990 | Liu |
| 5,773,710 | A | 6/1998 | Squirrell |
| 5,918,259 | A | 6/1999 | Squirrell |
| 6,051,189 | A * | 4/2000 | Wick et al. ............... 422/82.01 |
| 6,087,183 | A | 7/2000 | Zaromb |
| 6,103,534 | A | 8/2000 | Stenger et al. |
| 6,170,342 | B1 | 1/2001 | John |
| 6,231,645 | B1 * | 5/2001 | Conrad et al. ................. 95/271 |
| 6,514,721 | B2 | 2/2003 | Spurrell |
| 6,517,593 | B1 | 2/2003 | Robertson et al. |
| 6,531,066 | B1 * | 3/2003 | Saunders et al. ........... 210/787 |
| 6,532,835 | B1 | 3/2003 | Saaski et al. |
| 7,171,725 | B2 * | 2/2007 | Sjoberg et al. ............... 15/348 |
| 2001/0010189 | A1 * | 8/2001 | Conrad et al. ................. 95/271 |
| 2002/0124664 | A1 * | 9/2002 | Call et al. ................. 73/863.22 |
| 2004/0103785 | A1 * | 6/2004 | North .......................... 95/271 |
| 2005/0115409 | A1 * | 6/2005 | Conrad ........................ 95/271 |
| 2006/0144025 | A1 * | 7/2006 | Vallayer et al. ................ 55/428 |

FOREIGN PATENT DOCUMENTS

| | | | |
|---|---|---|---|
| JP | 2003144363 | * | 5/2003 |
| WO | WO 85/03571 | | 8/1985 |
| WO | WO 02/29380 | | 4/2002 |

OTHER PUBLICATIONS

Internet website, Home Diagnostics, "The Home Diagnostics Air Sampler," www.homediagnostics.net/products.asp (3 pages).

Internet website, SKC Inc., "WallChek Microbial Sampler," www.skcinc.info/instructions/1525.pdf (2 pages).

Internet website, G.O. Environmental, "PAQS Personal Air Quality Sampler," www.generaloceanics.com/genocean/paqs.htm (2 pages).

Internet website, F&J Speciality Products, Inc., "Personal Air Samplers and Accessories," www.fjspecialty.com/catalog/newitems/pas.htm (4 pages).

Internet website, Research Triangle Institute, "Personal Air Exposure Aerosol Sampler," www.clean.rti.org/aerosol/sampler.htm (1 page).

Internet website, SKC Gulf Coast, Inc., "Button Aerosol Sampler, Catalog No. 225-360" www.skcinc.info/instructions/3780.pdf (4 pages).

Internet website, Zefon International, Inc., "Air-O-Cell® Cassette, 50/pk" http://www.zefon.com/store/customer/product.php-?productid=1&cat=0&page= (3 pages).

Internet website, "Exposure to particles and biological responses," www.rikshospitalet.no/view/readforskat.asp?nPubID=759 (2 pages).

Internet website, Zaromb Research Corporation, "Portable High-Throughput Liquid Assisted Air Sampler (PHTLAAS)," http://www.zaromb.com/products.htm (2 pages) and "Rapid Sampling and Detection of Airborne Hazards," http://www.zaromb.com (2 pages).

Internet website, "Personal Air Sampler," http://www.jsits.com/geneq/en/pasamp/htm (2 pages).

Internet website, Monitoring Technologies Corporation, "Air Samplers," http://www.montec.com/htm/mtairsam.htm (12 pages).

Internet website, Burkard Manufacturing Co. Ltd. "Cyclone sampler for airborne particles," http://www.burkard.co.uk/cycsamp.htm (1 page).

Sales literature, Burkard Manufacturing Co. Ltd., "Cyclone Sampler for Airborne Particles," (2 pages).

Operating Instuctions for Cyclone Sampler for Airborne Particles, Burkard C90M (3 pages).

Internet website, Burkard Manufacturing Co. Ltd., "Continuous recording air sampler," http://www.burkard.co.uk/constas.htm (1 page).

Internet website, International pbi S.p.A, "Microbiological Air and Surface Samplers," http://www.labpbi.com/it040010.htm (3 pages).

Casagrande, R., "Technology Against Terror," Scientific American, Inc. pp. 83-87, Oct. 2002.

Chen et al., "Fungal Aerosols: Sampling and Analysis," abstract, Oct. 20, 2003.

Chen et al., "Development of a Personal Sampler for Collecting Fungal Spores," Aerosol Science and Technolog, 38:926-937 (2004).

Chen et al., "Fungal Spores: Sampling and Analysis," powerpoint presentation, presented at the Association of American Aerosol Research Annual Meeting, Oct. 20, 2003.

Chen et al., "Development of a Personal Bioaerosol Sampler," abstract, Jun. 2004.

Chen et al., "Development of a Personal Bioaerosol Sampler," powerpoint presentation, presented at the Scientific Conference on Obscuration and Aerosol Research, Edgewood, MA, Jun. 25-29, 2004.

Chen et al., "Microcentrifuge Tube Sampler," powerpoint presentation, presented at the Pan-American Aerobiology Association (PAAA) Conference, Jun. 20, 2004.

Dirgo and Leith, "Cyclone collection efficiency: comparison of experimental results with theoretical predictions," Aerosol Sci. Technol., 4:401-415 (1985).

Emberlin et al., "The development of a new method of sampling airborn particles for immunological analysis," XVI European Congress of Allergology and Clinical Immunology ECACI'95, pp. 39-43 (Jun. 1995).

Görner et al., "Study of Fifteen Respirable Aerosol Samplers Used in Occupational Hygiene," Ann. Occup. Hyg., 45(1):43-54 (2001).

Górny et al., "Fungal Fragments as Indoor Air Biocontaminants," Appl Environ Microbiol, 68(7):3522-3531, Jul. 2002.

Griffiths et al., "Computational Fluid Dynamics (CFD) and Empirical Modelling of the Performance of a Number of Cyclone Samplers," J. Aerosol Sci., 27(2):281-304 (1996).

Heal, MR et al., "Intercomparison of five PM10 monitoring devices and the implications for exposure measurement in epidemiological research," J Environ Monit., 2(5):455-61, Oct. 2000 (abstract only).

Kenny, LC et al., "The adaptation of existing personal inhalable aerosol samplers for bioaerosol sampling," Am Ind Hyg Assoc J., 59(12):831-41, Dec. 1998 (abstract only).

Kim and Lee, "Experimental study of particle collection by small cyclones," Aerosol Sci. Technol., 12:1003-1015 (1990).

Liden et al., "Comparison of measured respirable dust sampler penetration curves with sampling conventions," Ann Occup Hyg.,35(5):485-504, Oct. 1991 (abstract only).

McCartney et al. "Detecting Airborne Plant Pathogenic Fungal Spores by Polymerase Chain Reaction (PCR) Assays," Abstract, retrieved from http://ams.confex.com/ams/AugDavis/14BioAero/abstracts/15139.htm.

Rao et al., "Development of a Personal Bioaerosol Sampler," abstract, Jun. 2004.

Upton et al., "A wind tunnel evaluation of the physical sampling efficiencies of three bioaerosol samplers," J. Aerosol Sci., 25:1493-1501 (1994).

Williams et al., "Methods for Integrated Air Sampling and DNA Analysis for Detection of Airborne Fungal Spores," Applied and Environmental Microbiology, vol. 67, p. 2453-2459, Jun. 2001.

Yanosky, JD et al., "A comparison of four gravimetric fine particle sampling methods," J Air Waste Manag Assoc., 51(6):878-84, Jun. 2001 (abstract only).

Zhou et al., "Development of a fungus-specific PCR assay for detecting low-level fungi in an indoor environment," Molecular and Cellular Probes, 14:339-348 (2000).

Zhu et al., "Design and Performance Evaluation of a Novel Double Cyclone," Aerosol Science and Technology, 34:373-380 (2001).

Intelligent Optical Systems, Inc., Analytical Technology Division, "Micro-Optics Based Digital Allergen Counter," (2 pages).

International Search Report for corresponding PCT Application No. PCT/US2004/032378.

International Preliminary Report on Patentability for corresponding PCT Application No. PCT/US2004/032378.

Written Opinion of the International Searching Authority for corresponding PCT Application No. PCT/US2004/032378.

Internet website, Burkhard Manufacturing Co., Ltd., "Mycological/Entomological Instruments and Apparatus," www.burkard.co.uk/instmts.htm (3 pages).

Internet website, The BIOTEST (UK) Ltd., "The BIOTEST Reuter Centrifugal Sampler," www.medicine.mcgill.ca/epidemiology/theriault/molds/biotest.htm (1 page).

Internet website, "The Andersen Sampler," www.medicine.mcgill.ca/epidemiology/theriault/molds/Andersen.htm (1 page).

Internet website, AEA Technology, "Cyclone—Design of reverse cyclones," http://www.aeat.co.uk/pes/basys/environments/software/cyclone.htm (1 page) and "Cyclone Design Course," http://www.aeat.co.uk/pes/consult/training/cyclone.htm. (2 pages).

* cited by examiner

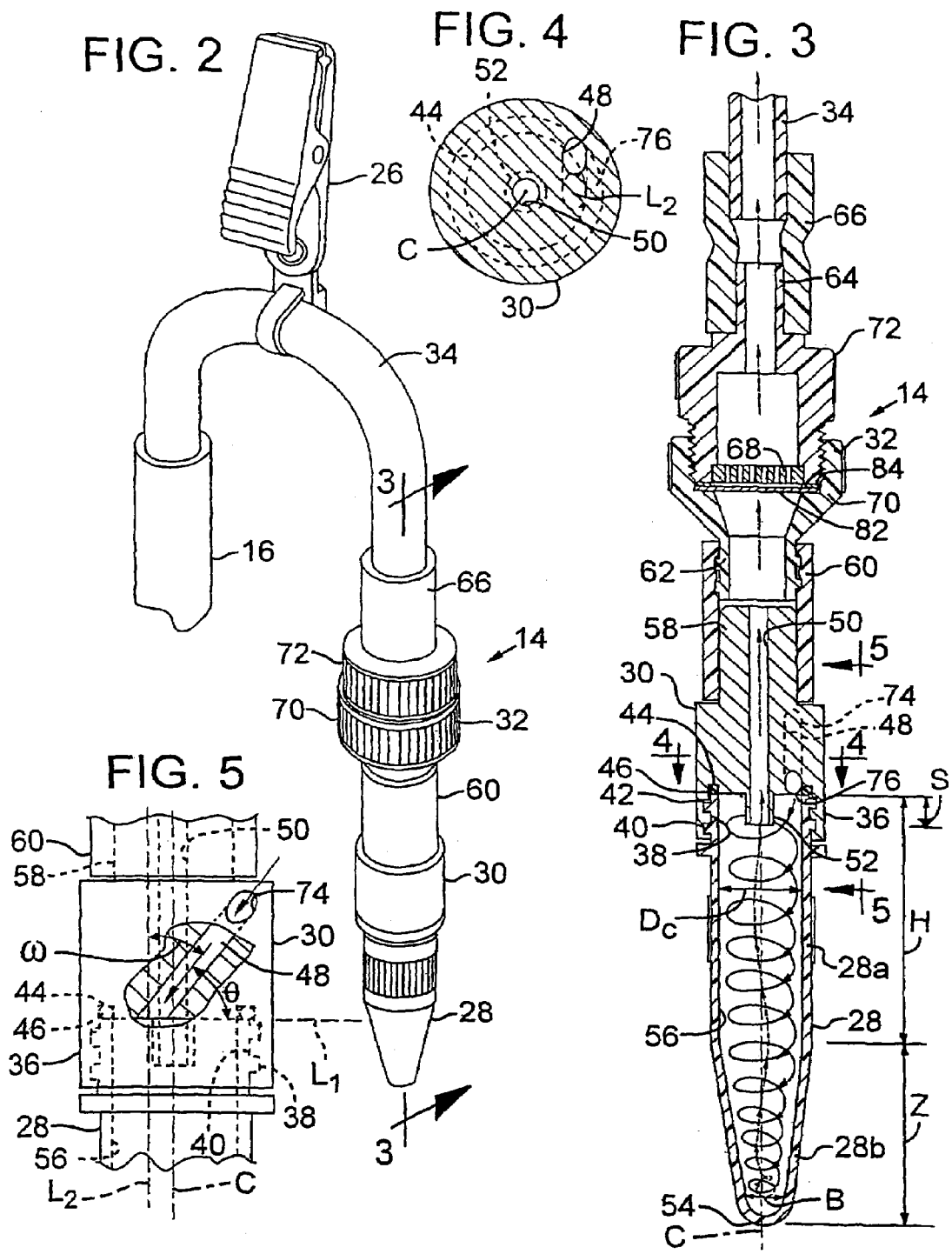

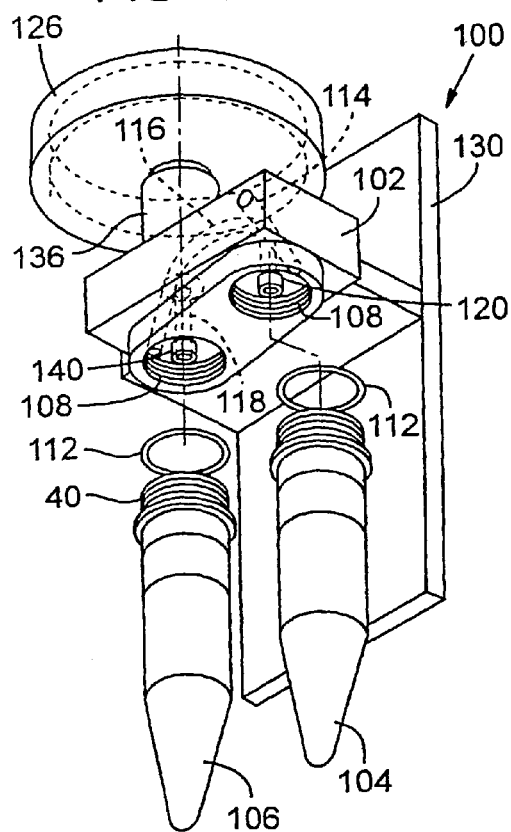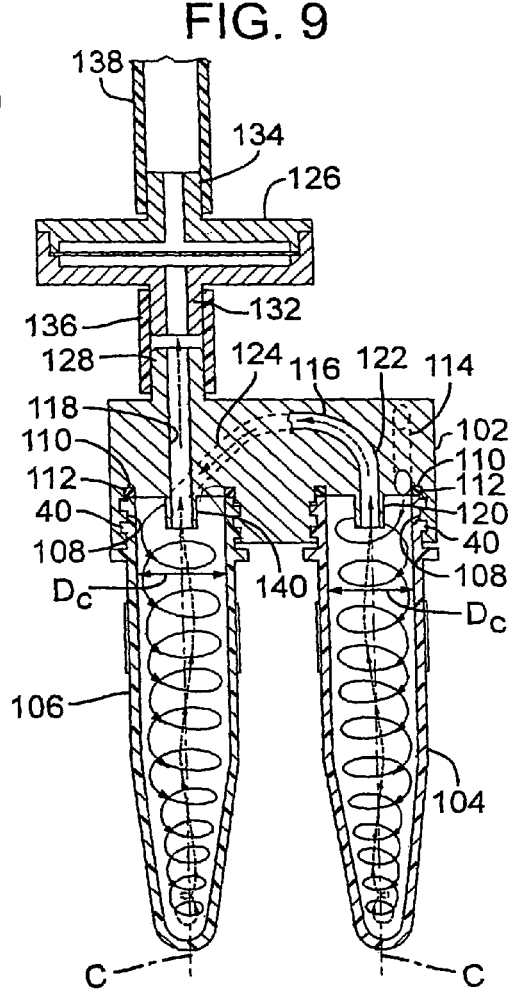

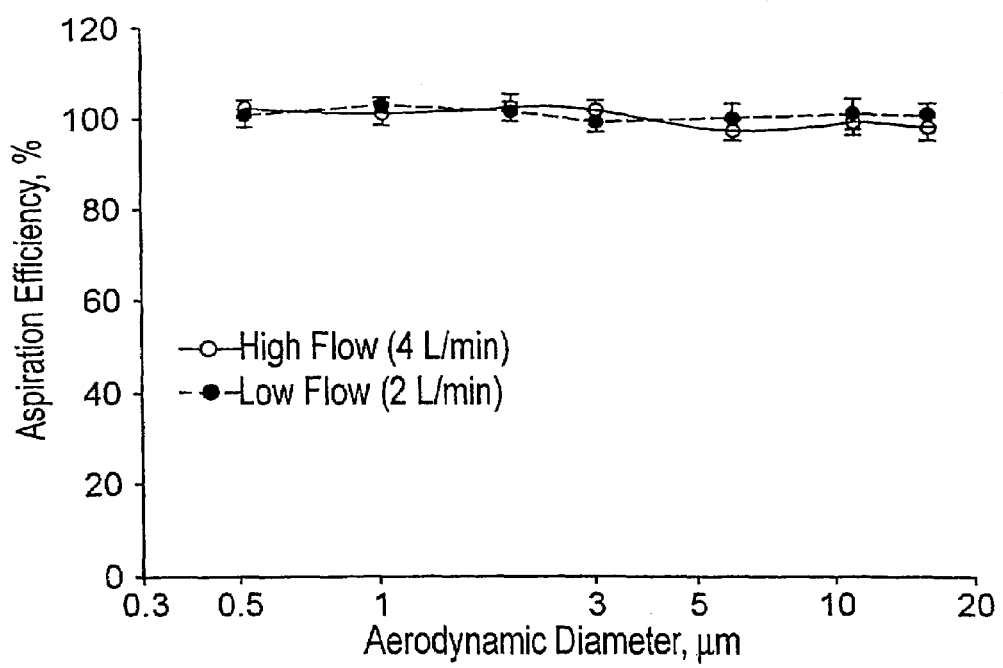

Collection Efficiency of the Microtube Sampler ($D_{in}$ = 2mm)
(Error Bar Represents +/- 1 SD; N = 6)

Particle Collection Efficiency in the Tube

AIR-SAMPLING DEVICE AND METHOD OF USE

CROSS REFERENCE TO RELATED APPLICATION

This is the U.S. National Stage of International Application No. PCT/US52004/032378, filed Oct. 1, 2004, which in turn claims the benefit of U.S. Provisional Application No. 60/512,252, filed Oct. 17, 2003. Both applications are incorporated herein by reference.

FIELD

The present invention concerns embodiments of a device for sampling airborne particles (aerosols), and methods for its use.

BACKGROUND

Air sampling is used to collect samples of airborne particles that are present in an environment. Analyses of the air samples can provide information concerning potential exposure to harmful respirable agents. Bioaerosol sampling can be used to identify particles of biological origin, such as, viable and non-viable fungal spores, bacteria, pollen, skin cells, fibers and insect parts.

Until recently, analyses of bioaerosol samples typically involved directly counting the organisms in a sample or indirectly by providing culture media in an environment and counting colony-forming units. While these methods provide reasonably adequate assessment of bioaerosol concentration, such methods are time consuming (e.g., some analyses may take days or even weeks to complete) and may be unreliable. Recently, the threat of biological warfare and terrorist attack has prompted the development of highly sensitive molecular techniques for detecting microorganisms, such as polymerase chain reaction (PCR) and immunological assays.

Sampling devices that are currently used for collecting bioaerosols for subsequent analysis include filters, impingers, and impactors. However, such devices suffer from disadvantages that limit their use in assessing exposure to airborne bioparticulates. For example, samples extracted from filters are often insufficient for determining the concentration of bioparticulates in the air because of poor extraction efficiency. Impingers and impactors may be suitable for short-term samplings; however, these devices cannot be used for long-term exposure assessment because of liquid evaporation in impingers and potential particle re-entrainment in impactors.

Hence, there is a need for new and improved devices for sampling airborne particles, and especially for sampling devices that can monitor ambient air for the presence of biowarfare pathogens, such as anthrax spores, potentially pathogenic mold in the environment, and other potentially hazardous bioparticulates.

SUMMARY

The present disclosure concerns embodiments of a sampling apparatus that utilizes one or more cyclone separators to collect airborne particles from the atmosphere. According to one aspect, the sampling apparatus employs a tube or other vessel that functions as both a cyclone separator to separate out aerosols from an air stream flowing through the tube and as a collection tube for collecting the separated aerosols.

When sampling an environment, air from the surrounding atmosphere is drawn through the open end of the collection tube. The air entering the tube is directed to flow in a direction that is generally tangential to the inner surface of the tube, which causes the air to spiral toward the closed end of the tube to form an outer vortex. The air flow then spirals back toward the open end of the tube to form an inner vortex and exits the tube through its open end. The velocity of the air flow exerts a centrifugal force on particles entrained in the air, causing them to impact the tube's inner surface and separate from the air flow. Since the sample is collected directly in the collection tube, in situ analysis of the collected particles can be performed. Some examples of analyses that can be performed on the collected sample include, without limitation, PCR, immunoassay analysis, microscopic spore counting, and counting colony-forming units.

The collection tube can be a conventional microcentrifuge tube, such as an Eppendorf® microcentrifuge tube, commonly used in laboratories for performing various processes such as, sonicating, homogenizing, and transferring samples. In certain embodiments, the collection tube is screwed onto or otherwise retained by a fitting that couples to the open end of the collection tube and functions to conduct air into and out of the collection tube. After a sampling period, the collection tube can be easily removed from the fitting for subsequent analysis of the collected sample. The fitting has an inlet passageway that conducts atmospheric air through the open end into the interior of the collection tube. An outlet passageway in the fitting allows air to escape the collection tube through its open end. A vacuum pump can be fluidly connected to the air outlet, such as with flexible tubing, to draw atmospheric air through the collection tube.

According to another aspect, the sampling apparatus may be a personal sampler that is of sufficiently small size so that it can be worn by a user to determine the quality of air being respirated. Alternatively, the sampling apparatus may be used as an area sampler such as for long term sampling of an environment.

In one representative embodiment, the sampling apparatus includes a collection-vessel retaining member that is adapted to be removably coupled to a collection vessel. The retaining member has an air-inlet conduit for permitting air to flow through the open end of the collection vessel and an air-outlet conduit for permitting air to exit the open end of the collection vessel. The air-inlet conduit and the air-outlet conduit are configured to cause air flowing into the collection vessel to establish a cyclonic flow path, which causes airborne particles to separate out from the air stream and collect in the collection vessel.

In particular embodiments, the retaining member may be adapted to couple to first and second collection vessels. The first collection vessel serves as a first-stage cyclone separator to separate aerosols from an air stream conducted into the first collection vessel via the air-inlet conduit. Air exiting the first collection vessel is conducted into the second collection vessel, which serves as a second-stage cyclone separator to further separate aerosols from the air stream.

In another representative embodiment, the sampling apparatus includes a collection vessel in which airborne particles are collected for analysis. An air-inlet conduit conducts air into the collection vessel and an air-outlet conduit conducts air out of the collection vessel. The air-inlet conduit extends in a direction that is non-orthogonal and non-parallel to a plane that is parallel to the open end of the collection vessel so as to cause air entering the collection vessel to flow generally tangentially with respect to the collection vessel inner surface and form a vortex for separating airborne particles.

In another representative embodiment, a method for analyzing airborne particles includes flowing untreated air into a collection vessel, establishing a double vortex in the collection vessel to cause airborne particles to separated out from the air and collect in the collection vessel, and performing an analysis of the collected particles. In some embodiments, the analysis is performed while the particles are still in the collection vessel. In other embodiments, the particles can be removed from the collection vessel prior to performing the analysis.

The foregoing and other features and advantages of the invention will become more apparent from the following detailed description of several embodiments, which proceeds with reference to the accompanying figures.

BRIEF DESCRIPTION OF THE DRAWINGS

FIG. 2 is an enlarged, perspective view of the sampling device of the apparatus shown in FIG. 1.

FIG. 3 is a vertical cross-sectional view of the sampling device taken along line 3-3 of FIG. 2.

FIG. 4 is a horizontal cross-sectional view of the retaining member of the sampling device taken along line 4-4 of FIG. 3.

FIG. 5 is an enlarged, elevation view of a portion of the sampling device shown in FIGS. 1-4.

FIG. 8 is a partially exploded, perspective view of a two-stage sampling device, according to one embodiment.

FIG. 9 is a vertical cross-sectional view of the sampling device shown in FIG. 8.

FIG. 10 is a graph showing the aspiration efficiency of a sampling device.

DETAILED DESCRIPTION

As used herein, the singular forms "a," "an," and "the" refer to one or more than one, unless the context clearly dictates otherwise.

As used herein, the term "includes" means "comprises."

As used herein, a group of individual members stated in the alternative includes embodiments relating to a single member of the group or combinations of multiple members. For example, the term "a, b, or c," includes embodiments relating to "a," "b," "c," "a and b," "a and c," "b and c," and "a, b, and c."

Figure 1:
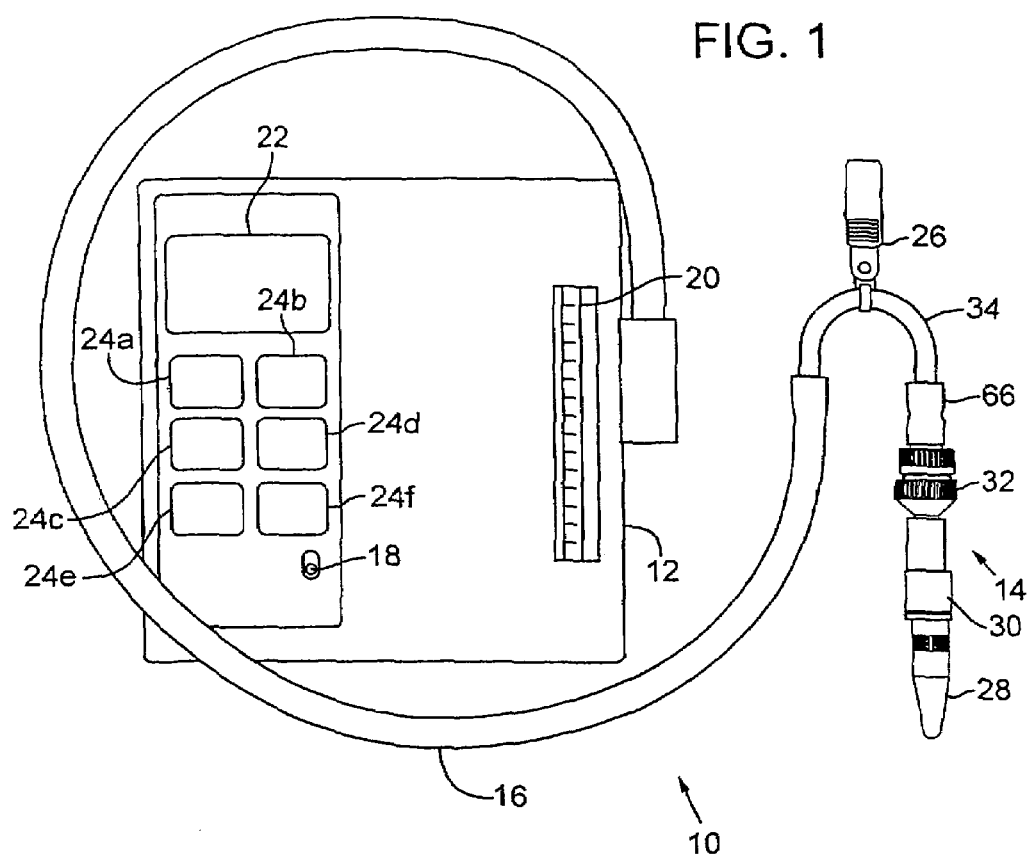
FIG. 1 shows an apparatus, according to one embodiment, for sampling airborne particles, such as bioaerosols.
Figure 6:
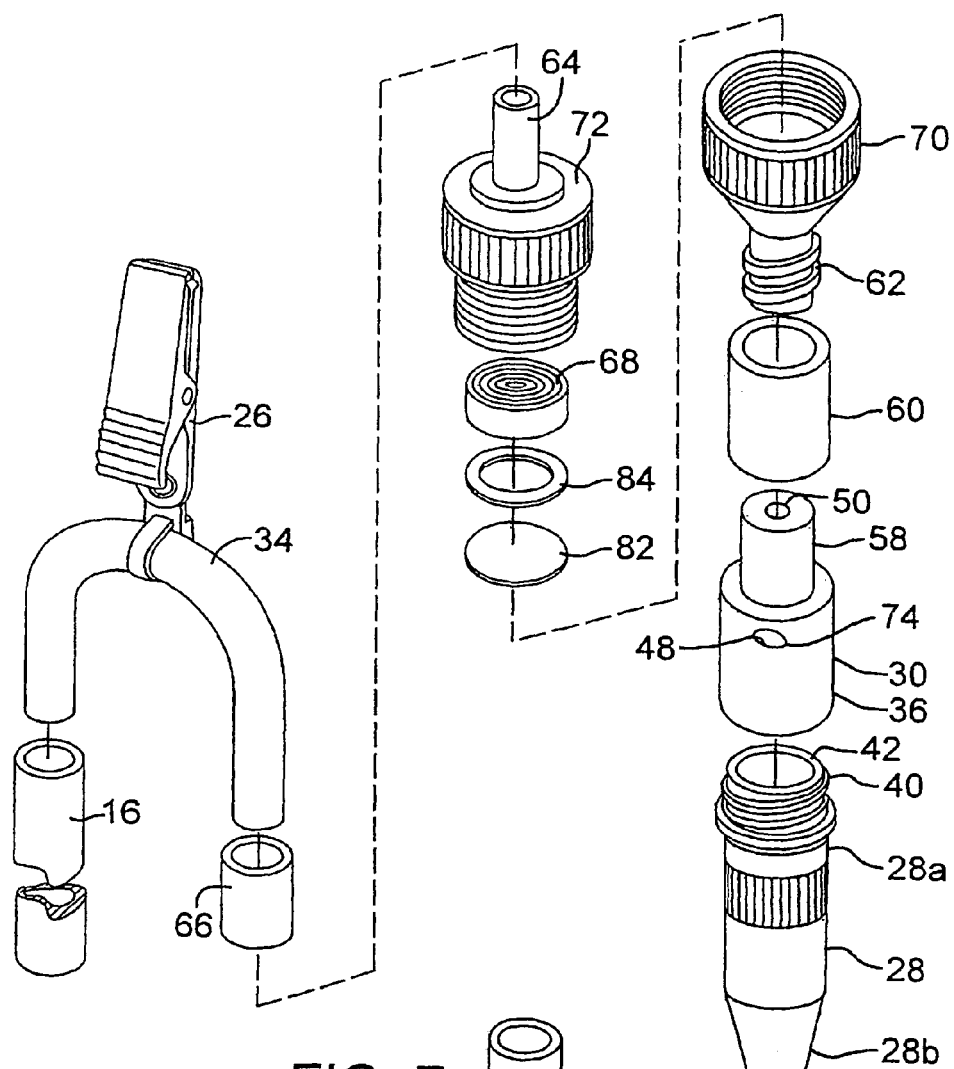
FIG. 6 is an exploded, perspective view of the sampling device shown in FIGS. 1-3.

Referring first to FIG. 1, there is shown one embodiment of an apparatus 10 for sampling airborne particles. The apparatus 10 in the illustrated configuration includes a control unit 12 that has an internal vacuum pump (not shown) that is fluidly connected to a sampling unit 14 (also referred to herein as a sampling device) via a fluid conduit 16 (e.g., Tygon® flexible tubing). The vacuum pump, under the control unit 12, draws a desired amount of air through the sampling unit 14 to create the necessary flow to separate airborne particles from the air. The vacuum pump (and other electrical components of the control unit 12) desirably receives power from an onboard battery storage system, such as rechargeable or replaceable batteries (not shown) for ease of portability and use. However, an external energy source can alternately provide power to control unit 12.

As shown in FIG. 1, the illustrated control unit 12 includes an ON/OFF power switch 18, a vacuum gauge 20, a display screen 22, which can be a liquid crystal display (LCD), and control buttons 24a, 24b, 24c, 24d, 24e, and 24f. Control buttons 24a-24f can be used to control different operating parameters of the control unit 12, such as flow rate, run time, and shut-off time, and/or to select certain parameters to be displayed on the display screen 22. In particular embodiments, the control unit 12 is a model 224-PCXR8, available from SKC Inc., of Eighty Four, Pa., although other commercially available devices also can be used.

In particular embodiments, the apparatus 10 is sufficiently lightweight and portable so that it can be worn by a user as a personal air sampler to determine the quality of air being respirated. In this regard, the sampling unit 14 can have a spring clip 26 or similar device for attaching the sampling unit 14 to a user's shirt or jacket. In use, the clip 26 desirably is attached to the collar of the user's shirt or jacket so that the atmosphere proximate the user's mouth can be monitored through the sampling unit 14. The control unit 12 desirably is relatively light and small, so that it can be placed or worn on a person's clothing. For example, the control unit 12 can be placed in a pocket or attached to a user's belt.

Referring to FIGS. 2 and 3, the sampling unit 14 in the illustrated configuration generally includes a collection vessel 28 (also referred to herein as a collection tube), a collection-vessel retaining member 30 (also referred to herein as an air-flow member and an air-flow fitting), a filter 32 (known as a "filter cassette"), and a piece of rigid tubing 34 to which the spring clip 26 is attached.

As best shown in FIG. 3, the illustrated collection vessel 28 has an upper cylindrical portion 28a formed with an open end 42 and a lower tapered portion 28b formed with a closed end 54 opposite the open end 42. The shape of the collection vessel is not limited to that shown in the illustrated embodiment; collection vessels having various other shapes also may be used. In one embodiment, for example, the collection vessel is generally cylindrical and has a substantially constant cross-sectional profile.

The collection vessel 28 desirably is designed to be removably coupled to a first end 36 of the retaining member 30. In the illustrated embodiment, for example, the first end 36 of the retaining member 30 is formed with a threaded opening 38 configured to mate with threaded portion 40 of the collection vessel 28 (as shown in FIG. 3). Thus, the collection vessel 28 can be easily mounted to the retaining member 30 by screwing the collection vessel 28 onto the threads 38 of the retaining member 30. After a sample is collected in the collection vessel 28, it can be easily unscrewed from the retaining member 30 to permit testing of the sample.

Alternative techniques or designs can be implemented to couple the collection vessel 28 to the retaining member 30. In one embodiment, for example, the first end 36 of the retaining member 30 can be formed with a smooth inner surface (without threads 38) that is dimensioned to frictionally retain a collection vessel that is pressed into the first end 36. Clamps and other types of fasteners also can be used to retain the collection vessel 28 on the retaining member 30.

As shown in FIG. 3, the retaining member 30 also can be formed with an annular groove 44 adjacent the open end 42 of the collection vessel 28. The groove 44 is dimensioned to receive a sealing member 46 to ensure a fluid-tight seal between the retaining member 30 and the collection vessel 28. The sealing member 46 can be a conventional O-ring made from any suitable material. A cap or lid (not shown) (e.g., a screw-on cap) can be used to cover the open end 42 of the collection vessel 28 after it is removed from the retaining member 30 to prevent spillage of the collected sample.

In certain embodiments, the collection vessel 28 is a conventional microcentrifuge tube (commonly known as Eppendorf® tubes), such as commonly used in molecular assays for performing various processes such as, sonicating, homogenizing, and transferring samples. Microcentrifuge tubes are commercially available from various manufacturers such as, Eppendorf AG of Hamburg, Germany; Sorenson Bioscience of Salt Lake City, Utah; Porex Inc. of College Park, Ga.; Coring Life Sciences of Acton, Mass.; and Simport Inc. of Beloeil, QC, Canada. Such tubes typically have a capacity of about 0.5 mL to 2.0 mL, although tubes having greater or lesser volume also may be used.

As shown in FIGS. 3-5, the retaining member 30 is formed with an air-inlet passageway or conduit 48 that permits air in the surrounding atmosphere to be drawn into the collection vessel 28 and an air-outlet passageway or conduit 50 that permit air to exit the collection vessel. The air-inlet passageway 48 includes an inlet 74 formed in the side of the retaining member 30 (as best shown in FIG. 5) and an outlet 76 (FIGS. 3 and 4) that opens to the interior of the collection vessel 28. In the illustrated embodiment, the air-inlet passageway 48 is laterally offset from a central axis C of the retaining member 30 with the outlet 76 being adjacent the inner surface of the collection vessel so that the air flow entering the collection vessel is generally tangential with respect to the inner surface of the collection vessel (as best shown in FIGS. 3 and 4). As shown in FIG. 5, the air-inlet passageway 48 also extends at an inclined angle θ relative to a line $L_1$ that is parallel to the open end 42 of the collection vessel 28. The air-inlet passageway 48 also defines an angle ω with respect to a line $L_2$ that is perpendicular to $L_1$ and parallel to but offset from the central axis C. Although variable, the angle θ of the air-inlet passageway 48 in particular embodiments is between about 30° and 45°, with 40° being a specific example.

In particular embodiments, the diameter of the air-inlet passageway 48 is between about 1 mm to 2 mm, with 1.99 mm being a specific example. The diameter of the air-outlet passageway 50 is between about 2 mm to 3 mm, with 2.24 mm being a specific example. Of course, these specific dimensions (as well as other dimensions provided in the present specification) are given to illustrate the invention and not to limit it. The dimensions provided herein can be modified as needed in different applications or situations.

As shown in FIG. 3, the air-outlet passageway 50 extends along the central axis C and opens to the interior of the collection vessel 28. The entrance of the air-outlet passageway 50 is defined by a centrally disposed extension portion 52 that extends a selected distance S (FIG. 3) into the open end 42 of the collection vessel 28. The extension portion 52 serves as a vortex finder to facilitate the formation of a vortex or cyclonic air-flow pattern in the collection vessel 28.

Air flowing through the air-inlet passageway 48 enters the collection vessel 28, spirals downwardly toward the closed end 54 to form an outer vortex, spirals upwardly generally within the outer vortex to form an inner vortex, and flows outwardly through the air-outlet passageway 50. This air-flow pattern is known as a "double vortex" or a "reverse-flow cyclone." Airborne particles that are generally larger than the cut-off size of the collection vessel impact the collection vessel inner surface 56 and separate from the air flow. The separated particles are deposited along the collection vessel inner surface 56 in a generally spiral configuration and/or migrate to the bottom of the collection vessel 28. In this manner, the collection vessel serves as a cyclone separator or cyclone device for separating out aerosols from the air stream, as well as a collection vessel for retaining the separated particles. Air exiting the collection vessel 28 flows through the air-outlet passageway 50, the filter 32, tubing 34, the fluid conduit 16, and into the vacuum pump (not shown), which exhausts the air to the atmosphere.

As generally known in the art, the performance or collection efficiency of a cyclone sampler at a given flow rate can be represented by the 50% cut-off point or cut-off diameter, $D_{50}$, of the sampler. The cut-off diameter $D_{50}$ is the aerodynamic diameter ($D_{ae}$) of the particle that is collected and retained by a sampler at a given flow rate with a 50% collection efficiency. For example, a sampler having a $D_{50}$ of 10 μm will collect and retain 50% of all particles equal to about 10 μm. Embodiments of the sampling unit 14 can achieve a cut-off diameter $D_{50}$ of less than 2 μm. Such embodiments are suitable for use in collecting airborne microorganisms, such as fungal spores. In addition, as demonstrated in the examples below, a small amount of water (e.g., 50-200 μL) or another suitable liquid can be placed in the collection vessel to increase its collection efficiency.

Referring again to FIG. 3, the retaining member 30 can be formed with a second end portion 58 having a reduced diameter. The second end portion 58 can be coupled to the filter 32 by a piece of flexible tubing 60 that extends over and forms a frictional fit with the second end portion 58 and a first end portion 62 of the filter 32. Similarly, a second end portion 64 of the filter 32 can be coupled to tubing 34 by a piece of flexible tubing 66 that extends over and forms a frictional fit with the second end portion 64 of the filter and tubing 34.

In certain embodiments, the filter 32 can be selected to have a filter media 68 suitable for filtering airborne particles that are generally smaller than the particles separated from the air flow in the collection vessel 28, if an analysis of such smaller particles is desired. In another embodiment, the filter is used to prevent particles of a certain size from flowing into and possibly damaging the vacuum pump (not shown). Thus, in the latter embodiment, it is not necessary that the filter be capable of filtering particles that are generally smaller than the particles separated from the air flow in the collection vessel 28. In yet another embodiment, the filter is not used.

Figure 7:
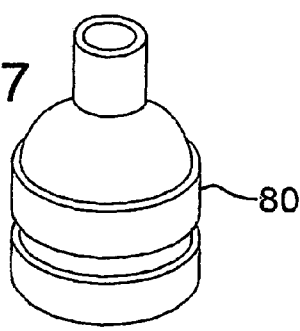
FIG. 7 is a perspective view of an alternative embodiment of a filter that can be used in the sampling device shown in FIGS. 1-3.

As shown in FIGS. 3 and 7, the filter 32 can include a porous member 82, which serves as a flow straightener and a support for the filter media 68, and an o-ring 84. In this embodiment, the filter media 68, the porous member 82, and the o-ring 84 are retained between first and second separable filter portions 70 and 72, respectively. If desired, the filter portions 70, 72 can be separated from each other to permit removal of the filter media 68 and analysis of the particles collected thereon. The filter portions 70, 72 can then be re-assembled with a new filter media 68.

FIG. 7 shows an alternative filter 80 that can be used in the sampling unit 14. While two specific examples of filters are illustrated in the figures, it can be appreciated that any of various commercially available filters (such as those available from SKC Inc. or BGI, Inc. of Waltham, Mass.) can be used in the sampling unit 14. Generally, the selection of the filter depends on the flow rate of the vacuum pump, the surrounding atmosphere in which a sample is to be collected, and the size of the particles that are to be removed from the air stream. Thus, it should be appreciated that the specific application will dictate the size of the filter to be used.

After a sampling period, the collection vessel 28 can be removed to perform one or more analyses on the collected particles. Some analyses, such as a PCR analysis, can be performed on the sample while it is in the collection vessel 28. Advantageously, this eliminates the possibility of sample loss, which can result from transferring the collected sample from the sampling device to a collection vessel, such as can happen when extracting a sample from a filter. If desired, a portion of the collected sample can be transferred to another collection vessel to perform a different type of analysis on the same sample. For example, a PCR analysis can be performed on the sample in one collection vessel and an immunoassay can be performed on the sample in another collection vessel. Of course, other types of analyses also can be used.

The sampling unit 14 can be used to detect for the presence of a specific type of aerosol, such as an airborne antigen, by placing in the collection vessel 28 an assay that is selected to react with such aerosol. To provide a visual indication of the presence of the aerosol, the assay can be selected to produce a color change upon reaction with the aerosol. In one implementation, the assay is placed in the collection vessel prior to collecting a sample. Thus, in this manner, the sampling unit provides a relatively quick and easy way to detect for the presence of a specific aerosol in real time while particles are being collected.

FIGS. 8 and 9 show a double-cyclone or two-stage sampling device 100, according to one embodiment. The sampling device 100 includes a collection-vessel retaining member 102 adapted to receive a first collection vessel 104 and a second collection vessel 106, which can be conventional microcentrifuge tubes. The sampling device 100 can also include an optional filter 126 to filter air flowing from the retaining member 102 to a vacuum pump (not shown in FIGS. 8 and 9). As shown in FIG. 8, the retaining member 102 can be coupled to a support member 130 that can be placed in a shirt pocket or attached to a user's clothing when the sampling device is used as a personal air sampler. The support member 130 can be provided with an adhesive or mechanical attachment device (e.g., spring clip) to permit attachment to the user's clothing.

The retaining member 102 can be formed with threaded openings 108 sized to receive the threaded portions 40 of the collections vessels 104, 106. The retaining member 102 also can be formed with annular groves 110 (FIG. 9) adjacent the threaded openings 108. Sealing members 112 are disposed in the annular groves 110 to establish a fluid-tight seal between the retaining member and the collection vessels.

In the illustrated embodiment, the retaining member 102 supports the collection vessels 104, 106 in the same orientation. In use, both collection vessels therefore can be positioned in a generally vertically upright orientation, such as shown in FIG. 9. This configuration is advantageous since it allows a liquid to be placed in one or both of the collection vessels. The liquid can be, for example, water placed in one or both collection vessels to increase collection efficiency or an assay selected to detect for the presence of a specific aerosol.

In other embodiments, the retaining member can be configured to support the collection vessels 104, 106 in different orientations. For example, one collection vessel can be supported at a 90° angle with respect to the other collection vessel. In another example, the collection vessels can be supported on opposite sides of the retaining member.

As best shown in FIG. 9, the retaining member 102 is formed with an inlet fluid passageway 114 for conducting air into the first collection vessel 104, an intermediate fluid passageway 116 for conducting air from the first collection vessel 104 to the second collection vessel 106, and an outlet fluid passageway 118 for conducting air out of the second collection vessel 106. The intermediate fluid passageway 116 therefore serves as an outlet fluid passageway for the first collection vessel 104 and an inlet fluid passageway for the second collection vessel 106. The retaining member 102 can be formed with extension portions 120 and 140 that define the entrance of the intermediate fluid passageway 116 and the outlet fluid passageway 118, respectively, and function as a vortex finders for the first and second collection vessels 104, 106.

The inlet fluid passageway 114 extends at an inclined angle (e.g., 40°) with respect to the open end of the first collection vessel 104 and introduces air through the open end of the first collection vessel 104 in a generally tangential direction with respect its inner surface to facilitate the formation of a vortex. As best shown in FIG. 9, the intermediate fluid passageway 116 in the illustrated embodiment includes a first portion 122 that extends upwardly from extension portion 120 and a second portion 124 that extends back downwardly and opens into the second collection vessel 106. The second portion 124 extends at an inclined angle (e.g., 40°) with respect to the open end of the second collection vessel 106 and introduces air through the open end of the second collection in a generally tangential direction with respect to its inner surface to facilitate the formation of a vortex therein. The intermediate fluid passageway 116 desirably traces a smooth, curved pathway between the two collection vessels to minimize particle retention on the inner surface of the intermediate fluid passageway.

The filter 126 can be coupled to the retaining member in any suitable manner. In the illustrated embodiment, the filter 126 has inlet portion 132 and an outlet portion 134. The inlet portion 132 is coupled to an extension portion 128 of the retaining member 102 with a piece of flexible tubing 136. The outlet portion 134 of the filter can be fluidly connected to a vacuum pump (not shown) via tubing 138.

In use, air is drawn into the first collection vessel 104 through the inlet fluid passageway 114 and forms a double vortex to separate airborne particles that are generally larger than the cut-off diameter of the first collection vessel. Air from the first collection vessel flows through the intermediate fluid passageway 116 into the second collection vessel 106. Air flowing into the second collection vessel 106 forms a double vortex to separate airborne particles that are generally larger than the cut-off diameter of the second collection vessel. The cut-off diameter of the first collection vessel can be the same as or different from the cut-off diameter of the second collection vessel.

The cut-off diameter of a collection vessel depends on at least the following parameters: the flow rate, the inside diameter $D_c$ of the collection vessel, and the diameter $D_i$ of the inlet conduit that conducts air into the collection vessel.

In the illustrated embodiment, the dimensions $D_c$ and $D_i$ for the first and second collection vessels. Hence, the first and second collection vessels have approximately the same cut-off diameters at the same flow rate. Since airborne particles are forced to flow through vortexes in two collection vessels, the overall particle collection efficiency of the sampling device is greater than the one-stage sampling device 14 shown in FIGS. 1-6. Thus, the two-stage embodiment may be used in situations where the analysis to be performed on the collected sample calls for a collection efficiency that is greater than the collection efficiency of the one-stage embodiment (although the one-stage embodiment provides a collection efficiency that is sufficient for most applications).

Another advantage of the two-stage embodiment is that two separate particle analyses can be performed on the collected samples while avoiding possible contamination or sample loss that can occur from sample transfer. In some applications, for example, it may be desirable to perform different types of analyses on the samples collected in the first and second collection vessels. Alternatively, in other applications, it may desirable to perform the same type of analysis on both samples to verify the accuracy or repeatability of such analysis.

In another implementation of the two-stage embodiment, an assay can be placed in one or both of the first and second collection vessels prior to sample collection. The assay in each collection vessel is selected to detect and provide a visual indication of the presence of a specific type of aerosol, such as by producing a color change, while particles are being collected in the collection vessels.

In an alternative embodiment, the cut-off diameters of the first and second collection vessels 104, 106 are sized such that the particles collected in the first collection vessel are generally larger than the particles collected in the second collection vessel. This can be achieved by providing a first collection vessel having an inside diameter $D_c$ that is greater than the inside diameter of the second collection vessel and/or by providing the first collection vessel with a inlet conduit having a diameter that is greater than the diameter of the inlet conduit to the second collection vessel (i.e., the diameter of conduit 114 would be greater than the diameter of second portion 124 of the intermediate conduit 116). The filter 126 also may be used to further separate out and collect particles that are smaller than the cut-off diameter of the second collection vessel. In this manner, the sampling device functions as a three-stage separation device (two cyclone stages and one filter stage).

In one embodiment, for example, the inlet conduit 114 to the first collection vessel has a diameter of about 1.99 mm, the second portion 124 of the intermediate conduit has a diameter of 1.3 mm, and the first and second collection vessels have an inside diameter $D_c$ of about 8.27 mm. At a flow rate of about 4 L/min, the first stage (i.e., the first collection vessel) achieves a cut-off diameter $D_{50}$ of about 1.5 μm and the second stage (i.e., the second collection vessel) achieves a cut-off diameter $D_{50}$ of about 0.8 μm.

In one application of the two-stage embodiment, the sampling device is operated at a flow rate such that the first collection vessel has a cut-off diameter of about 2 μm for collecting fungal spores and the second collection vessel has a cut-off diameter of about 0.5 μm for collecting bacterial spores. If desired, the filter 126 can be sized to separate out even smaller particles from the air flow.

In a similar application, the two-stage embodiment can be used to detect or measure the concentration of hazardous respirable particles, such as those attributable to coal dust, in a mining environment. In this application, the first collection vessel is selected to separate out particles approximately 10 μm and larger (which are considered to be non-hazardous in most industrial environments) and the second collection vessel is selected to separate out hazardous respirable particles ranging from approximately 0.8 μm to 10 μm. The filter 126 also may be used to separate out particles smaller than 0.8 μm to assess exposure to diesel exhaust particles.

While the illustrated retaining member 102 has a unitary or one-piece construction, other configurations are possible. For ease of manufacturing, the retaining member 102 can be made from two separately formed pieces that are joined together. For example, the retaining member can be made from left and right halves that are joined at a vertical plane extending between the collection vessels 104, 106.

In alternative embodiment, the first and second collection vessels are coupled to respective first and second retaining members, each having a respective air inlet and air outlet. The air outlet of the first retaining member is fluidly connected to the air inlet of the second retaining member, such as via a piece of tubing, so that air flows from the first collection vessel, through the outlet of the first retaining member, the inlet of the second retaining member, and into the second collection vessel.

EXAMPLES

Example 1

This example illustrates the performance of six sampling devices having the one-stage configuration shown in FIGS. 1-6. Each sampling device is similar in construction, although a different microcentrifuge tube is used as the collection vessel in each device. Table 1 below summarizes the $D_c$, H, Z, and B dimensions (FIG. 3) of the microcentrifuge tubes (identified as tubes a, b, c, d, e, and f). The total height (H and Z) of each tube is approximately 44 mm±1 mm. The retaining members of the sampling devices were fabricated to have an inlet diameter, $D_i$, of 1.99 mm, an outlet diameter, $D_o$, of 2.24 mm, an "S" dimension (FIG. 3) of 2.91 mm, and an inclination angle θ (FIG. 3) of approximately 40°. Each sampling device 14 included a filter having a 13-mm glass-fiber filter element. Table 2 below summarizes the physical parameters of the sampling devices and of the air flow through the sampling devices at 2 L/min and 4 L/min.

TABLE 1

| Collection tube | Part #/ Manufacturer | Capacity, mL | Type | $D_c$, mm | H, mm | Z, mm | B, mm |
|---|---|---|---|---|---|---|---|
| a | PGC 16-8117-06* Sorenson Bioscience | 2.0 | Self Stand | 8.35 ± 0.01 | 41.13 ± 0.05 | 3.02 ± 0.18 | 0 |
| b | PGC 16-8117-28* Sorenson Bioscience | 1.7 | Conical | 8.31 ± 0.01 | 26.49 ± 0.20 | 18.42 ± 0.21 | 3.02 ± 0.09 |
| c | PGC 16-8115-24* Porex 515 | 1.5 | Conical | 8.27 ± 0.03 | 24.48 ± 0.19 | 19.09 ± 0.32 | 2.99 ± 0.10 |
| d | COR 430909 Corning | 1.5 | Conical | 8.16 ± 0.01 | 25.62 ± 0.17 | 18.24 ± 0.17 | 2.94 ± 0.08 |
| e | SIM T334-5 Simport | 1.5 | Conical | 8.19 ± 0.03 | 25.76 ± 0.17 | 18.30 ± 0.20 | 2.96 ± 0.12 |
| f | SIM T334-7 Simport | 2.0 | Self Stand | 8.22 ± 0.05 | 39.39 ± 0.22 | 4.35 ± 0.23 | 0 |

*Indicates the part number given by PGC Scientific Co. of Gaithersburg, MD.

TABLE 2

| $D_i$, mm | $D_o$, mm | S, mm | θ, degree | Q, L/min | $V_i$, m/sec | $Re_{flow}$ |
|---|---|---|---|---|---|---|
| 1.99 | 2.24 | 2.91 | 40.0 | 2.0 | 10.72 | 1421.87 |
|  |  |  |  | 4.0 | 21.43 | 2843.75 |

In this example, as well as in the examples below, the sampling devices were operated in a calm-air chamber system. Monodisperse fluorescent-tagged polymer microspheres (Duke Scientific, Palo Alto, Calif.) having nominal aerodynamic diameters, $D_P$, between 0.51 and 16 μm were aerosolized and introduced into the chamber using either a liquid nebulizer (available from Hospitak Inc. of Farmingdale, N.Y., as catalog No. 952) or a dry-powder venturi disperser (In-Tox Products, Albuquerque, N. Mex.). When the nebulizer was used, a diffusion dryer having a desiccant and a clean, dry air flow were employed to remove water droplets in the aerosol. When the venturi was used, a solenoid valve was employed to create a pulsating air flow into the chamber to assist in dispersing the particles. The mean flow rate into the chamber was about 27.5 L/min. An automobile air filter was placed at the top of the chamber to dampen the overflow and maintain the calm-air condition in the chamber. An aerodynamic particle sizer (model No. 3320, available from TSI, Inc. of St. Paul, Minn.) was used to monitor the monodispersity of the aerosols in the chamber.

The sampling devices were operated in the chamber at flow rates of 2 L/min and 4 L/min and exposed to an atmosphere containing 1.94-μm particles. Following a sampling period, the sampling devices were removed from the chamber and the fluorescent intensity of the particles collected on the collection tube, retaining member, and filter of each sampling device was measured using a spectrofluorimeter (model C-60 from Photo Technology International, Monmouth Junction, N.J.) to determine the fractional deposition of particles on each part. Table 3 below shows the particle deposition of 1.94-μm particles on the collection tube, retaining member, and filter for each sampling device. As shown, the collection efficiency of 1.94-μm particles (i.e., the percentage of particles retained in the collection tubes) varies from 13.9% to 20.3% at 2 L/min and from 65.3% to 78.4% at 4 L/min. Tubes c, d, and e achieved higher efficiencies than tubes a, b, and f.

TABLE 3

(Fractional deposition of 1.94-μm particles).

| | | Fractional Deposition, % | | | |
|---|---|---|---|---|---|
| | | Q = 2 L/min | | Q = 4 L/min | |
| Tube | Sampler Part | Mean | Standard error, N = 1 | Mean | Standard error, N = 1 |
| a | Filter | 83.3 | 1.3 | 17.3 | 0.4 |
|  | Tube | 13.9 | 1.3 | 69.0 | 0.4 |
|  | Attachment | 2.7 | 0.2 | 13.6 | 0.1 |
| b | Filter | 77.0 | 1.8 | 18.3 | 0.7 |
|  | Tube | 18.7 | 1.8 | 65.3 | 1.0 |
|  | Attachment | 4.3 | 1.0 | 16.4 | 0.4 |
| c | Filter | 71.9 | 1.4 | 10.4 | 1.1 |
|  | Tube | 20.7 | 1.5 | 78.4 | 1.6 |
|  | Attachment | 7.4 | 1.6 | 11.3 | 1.5 |
| d | Filter | 75.1 | 1.1 | 12.7 | 1.0 |
|  | Tube | 20.0 | 1.9 | 73.3 | 1.7 |
|  | Attachment | 4.9 | 0.8 | 14.0 | 0.7 |
| e | Filter | 75.9 | 0.7 | 14.2 | 1.3 |
|  | Tube | 20.3 | 0.4 | 72.4 | 1.1 |
|  | Attachment | 3.7 | 0.5 | 13.4 | 0.9 |
| f | Filter | 77.4 | 1.2 | 17.0 | 0.5 |
|  | Tube | 18.4 | 1.0 | 69.8 | 0.9 |
|  | Attachment | 4.2 | 0.4 | 13.2 | 0.6 |

Example 2

Using tubes c, d, and e from Table 1, sampling devices were operated in the chamber at flow rates of 2 L/min and 4 L/min and exposed to atmospheres containing particles having nominal diameters of 0.51, 1, 1.94, 3, 6, 11, and 16 μm. Table 4 below shows the operating parameters and fractional deposition of particles for the sampling device used with tube c. The results obtained for the sampling devices used with tubes d and e were similar to the results shown in Table 4. The aspiration efficiency (the total percentage of airborne particles flowing through a sampler that are collected on the filter, collection tube, and retaining member) of the sampling devices, which is shown in FIG. 10, varied between 97% and 102%.

TABLE 4

(Fractional deposition of 0.51, 1.00, 1.94, 3.00, 6.00, 11.00, and 16.00-μm particles).

| $D_p$, μm | $D_{ae}$, μm | $Q_{avg}$, L/min | $V_i$, m/sec | $Re_{flow}$ | Stokes No. | Fractional deposit, % | | |
|---|---|---|---|---|---|---|---|---|
| | | | | | | Filter | Tube | Attachment |
| 0.51 | 0.52 | 2.02 | 10.73 | 1431 | 0.01 | 98.51 | 1.11 | 0.38 |
| | | 4.04 | 21.42 | 2856 | 0.02 | 92.93 | 4.67 | 2.40 |
| 1.00 | 1.03 | 2.04 | 10.84 | 1445 | 0.04 | 94.01 | 2.66 | 3.33 |
| | | 4.02 | 21.35 | 2847 | 0.08 | 80.99 | 14.91 | 4.10 |
| 1.94 | 1.99 | 2.03 | 10.75 | 1434 | 0.14 | 75.59 | 19.84 | 4.57 |
| | | 4.05 | 21.47 | 2863 | 0.28 | 15.02 | 71.53 | 13.44 |
| 3.00 | 3.08 | 2.05 | 10.88 | 1451 | 0.33 | 23.83 | 63.99 | 12.18 |
| | | 4.05 | 21.46 | 2862 | 0.66 | 0.98 | 97.48 | 1.54 |
| 6.00 | 6.15 | 2.06 | 10.90 | 1454 | 1.30 | 1.60 | 93.76 | 4.63 |
| | | 4.05 | 21.48 | 2865 | 2.57 | 0.33 | 98.64 | 1.03 |
| 11.00 | 11.27 | 2.08 | 11.05 | 1473 | 4.38 | 0.54 | 97.96 | 1.50 |
| | | 4.05 | 21.46 | 2862 | 8.51 | 0.18 | 99.05 | 0.77 |
| 16.00 | 16.40 | 2.05 | 10.88 | 1450 | 9.08 | 0.52 | 97.90 | 1.57 |
| | | 4.05 | 21.47 | 2863 | 17.93 | 0.19 | 99.16 | 0.66 |

Figure 11:
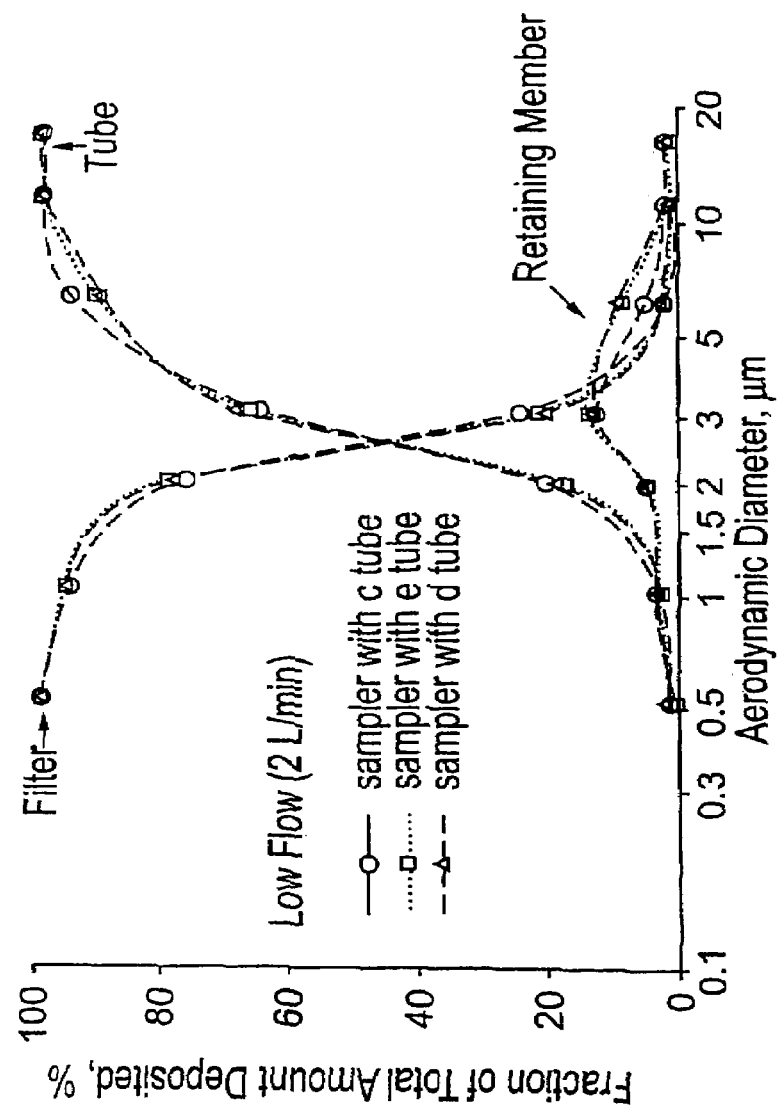
FIG. 11 is a graph showing the particle deposition in the collection tube, retaining member and filter of three sampling devices at a flow rate of 2 L/min.
Figure 12:
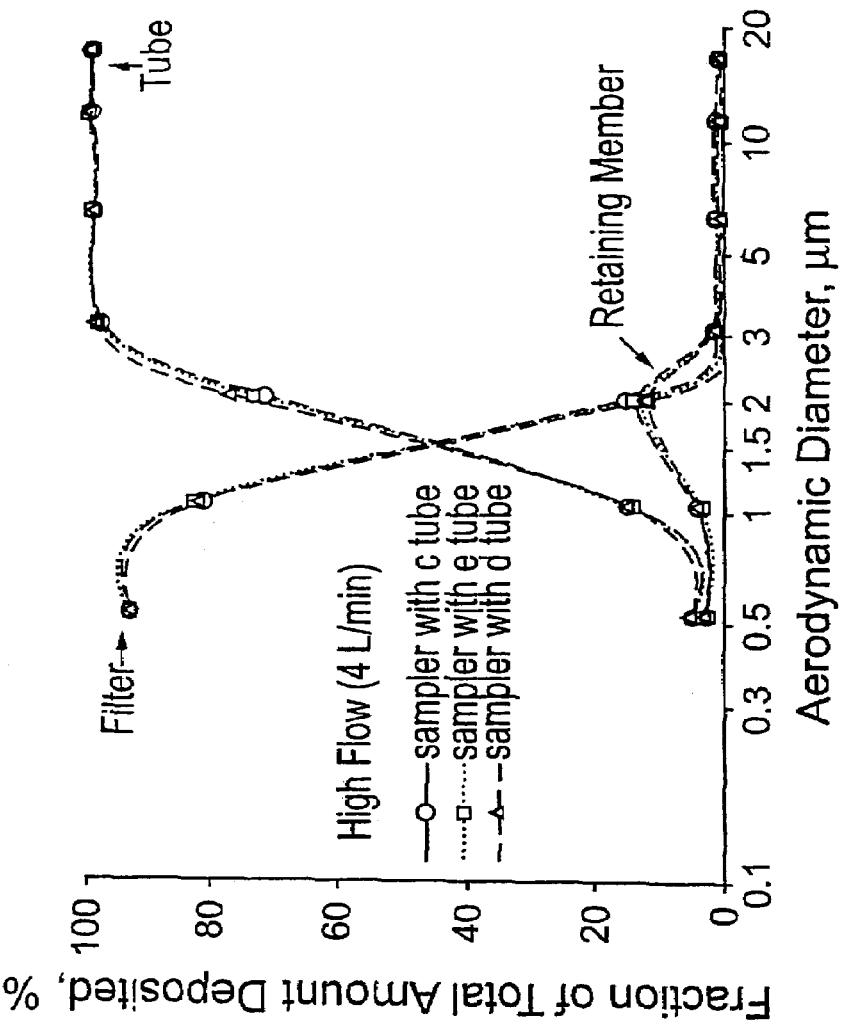
FIG. 12 is a graph showing the particle deposition in the collection tube, retaining member and filter of three sampling devices at a flow rate of 4 L/min.

FIGS. 11 and 12 are graphs showing the fraction of total particles deposited on the filter, collection tube, and retaining member of each sampling device at 2 L/min and 4 L/min, respectively. The "filter" curves correspond to the percentage of particles that penetrate the cyclones and collect on the filters. The "retaining member" curves correspond to the percentage of particles that are retained on the internal surfaces of the retaining members, and therefore is representative of the internal wall-losses of each sampling device. The "tube" curves correspond to the percentage of particles collected in the collection tubes (termed collection efficiency). As shown in FIGS. 11 and 12, the results for each sampling device are substantially similar. For each sampling device, the collection efficiency increased with particle size, ranging from about 1% for 0.5-μm particles to about 99% for 16-μm particles.

Figure 13:
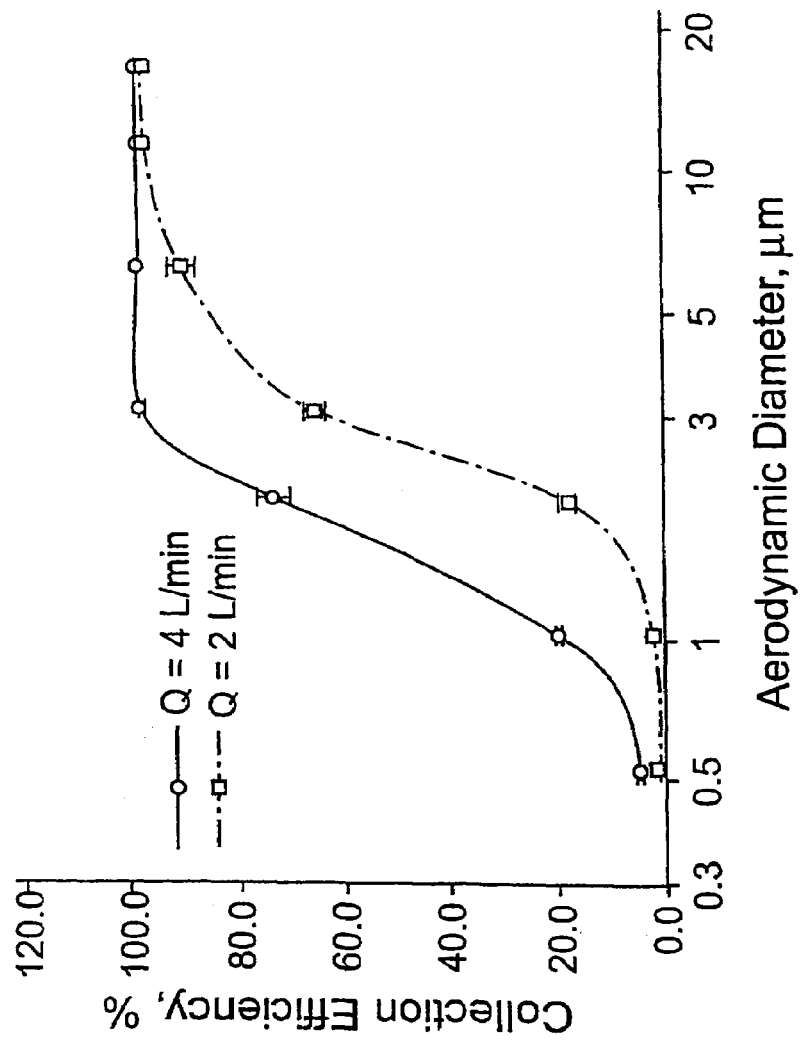
FIG. 13 is a graph showing the collection efficiency of a sampling device.
Figure 14:
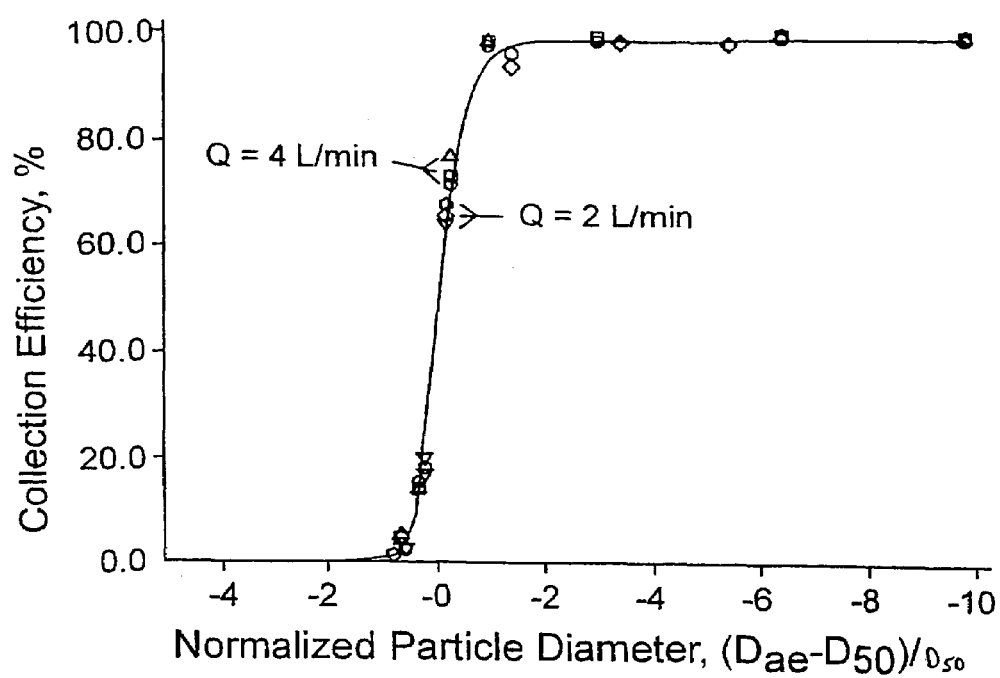
FIG. 14 is a graph of the collection efficiency of a sampling device as a function of normalized particle diameter.
Figure 15:
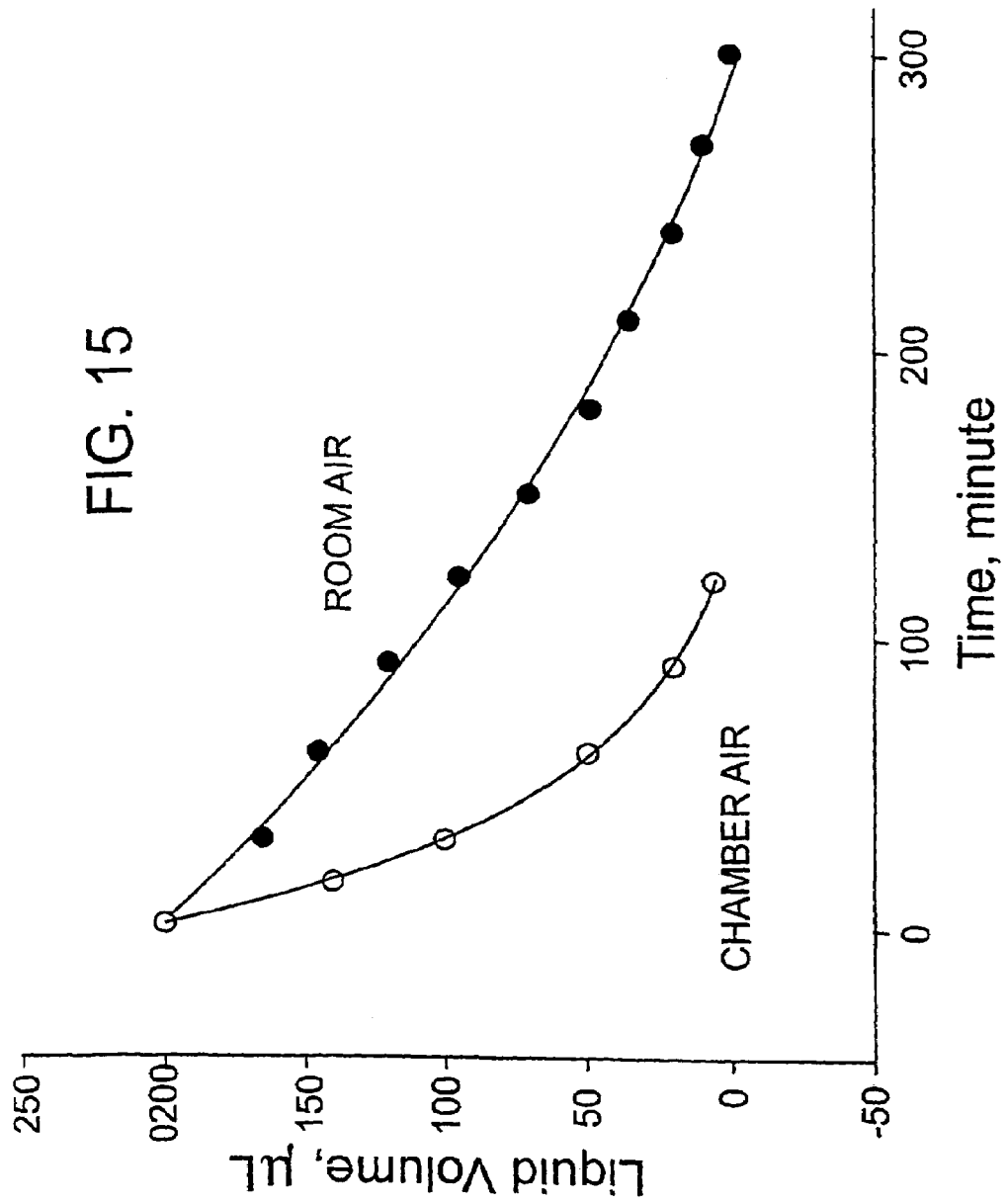
FIG. 15 is a graph showing the evaporation rate of water contained in a sampling device when operating within a testing chamber and outside the testing chamber.

FIG. 13 shows the collection efficiency curves of FIGS. 11 and 12 placed side-by-side for comparison (the curves at each flow rate are consolidated as one curve in FIG. 13). As shown, as the flow rate increases, the curve shifts to the left, indicating that there is a decrease in the 50% cut-off diameter $D_{50}$ as the flow rate increases. Specifically, the 50% cut-off diameter $D_{50}$ is approximately 2.5 μm at 2 L/min and approximately 1.5 μm at 4 L/min. In addition, the collection efficiency is greater than 90% at a flow rate of at least 4 L/min for particles greater than 2.5 μm, which is the size of most fungal spores found in indoor environments. In FIG. 14, the efficiency curves at 2 L/min and 4 L/min are consolidated into a single curve that plots collection efficiency against the normalized particle diameter, $(D_{ae}-D_{50})/D_{50}$.

For a sampling device having dimensions $D_c$, $D_i$, $D_o$, and S (FIG. 3) of 8.3 mm, 1.992 mm, 2.241 mm; 2.905 mm, respectively, the data shown in FIGS. 11-13 can be fitted to the following equation for the 50% cut-off diameter $D_{50}$:

$$D_{50} = e^a D_c^b Q^{1-b},$$

where Q is the sampling flow rate in L/min and the constants a and b are 1.7508 and 1.7370, respectively, which are determined using non-linear least-squares regression. This equation can be used to predict the collection efficiency of the sampling device at different flow rates.

Example 3

In this example, the internal surfaces tubes of c, d, and e (two of each), were coated with polyethylene glycol and then used to sample 1.94-μm particles in the chamber. Table 5 below shows the mean collection efficiency of each tube configuration at 2 L/min and 4 L/min with and without the polyethylene glycol. At 2 L/min, the mean collection efficiency for each tube with the coating was slightly higher than the mean collection efficiency of the same tube without the coating.

TABLE 5

(Collection efficiency for 1.94-μm particles on coated and uncoated collection vessels).

| | | Tube Collection Efficiency, % (Mean ± SE, N = 4) | |
|---|---|---|---|
| Tube | Flow Rate | Uncoated | Coated |
| c | 2 L/min | 19.8 ± 0.8 | 22.5 ± 3.9 |
| | 4 L/min | 71.5 ± 1.8 | 69.8 ± 0.9 |
| d | 2 L/min | 18.0 ± 0.7 | 20.6 ± 1.2 |
| | 4 L/min | 76.9 ± 0.9 | 71.9 ± 1.4 |
| e | 2 L/min | 17.0 ± 1.0 | 19.1 ± 0.5 |
| | 4 L/min | 73.3 ± 1.2 | 71.4 ± 0.8 |

Example 4

This example illustrates the evaporation rate of water from a collection vessel and how the presence of a liquid affects the collection efficiency of the cyclone sampling device.

To determine the evaporation rate from a collection tube, about 200 μL were placed in the collection tube of a sampling device, which was then was operated at a flow rate of 4 L/min outside of the chamber in an ambient environment for about 3 hours. The upper curve in FIG. 16 is a plot of the evaporation rate of water from the collection tube of sampling device operated outside of the chamber. As shown, about 145 μL remained in the collection tube after one hour of operation and about 95 μL remained in the collection tube after two hours of operation.

For comparison, this procedure was repeated but the sampling device was operated inside the chamber (without particles being introduced into the chamber). The lower curve in FIG. 16 is a plot of the evaporation rate of water from the collection tube of sampling device operated inside the chamber. The lower curve displays a much faster evaporation rate than the upper curve due to the fact that the relative humidity of the chamber air (about 7%-8%) was much lower than the relative humidity of the air outside of the chamber (about 45%-50%).

To demonstrate the effect that water has on the collection efficiency of a sampling device, three sampling devices, each having one of tubes c, d, and e filled with about 200 μL of distilled water, and three additional sampling devices, each having one of tubes c, d, and e without water, were positioned inside the chamber. The sampling devices were used to sample 1.00-μm particles for about 1 hour at a flow rate of 4 L/min. After the sampling period, the sampling devices were removed from the chamber and the fractional particle deposition on the filter, collection tube, and retaining member of each sampling device were measured. This procedure was repeated two more times, once using 1.94-μm particles and once using 3.00-μm particles. Table 6 below shows the percentage of particles deposited on the filter, collection tube, and retaining member of each sampling device for the three particle sizes. In each case, the presence of water resulted in a greater percentage of particles being collected in the collection tube. This indicates that placing a liquid in a collection tube allows the sampling device to achieve a smaller cut-off diameter $D_{50}$. Also, the percent contribution of the liquid in the total tube intensity varied from 6.05% for 1.00-μm particles to 10.16% for 3.00-μm particles. This data demonstrates that the particles collected in the tube would produce a noticeable color change of an immunoassay contained in the tube.

TABLE 6

| | | Fractional Deposition, % | | | | | | | | |
|---|---|---|---|---|---|---|---|---|---|---|
| | | 1.00 μm | | | 1.94 μm | | | 3.00 μm | | |
| Tube | Sampler Part | No liquid | With liquid | Percent in liquid* | No liquid | With liquid | Percent in liquid* | No liquid | With liquid | Percent in liquid* |
| c | Filter | 78.67 | 73.92 | | 13.06 | 9.83 | | 0.97 | 0.55 | |
| | Tube | 14.00 | 19.06 | 6.05 | 73.55 | 79.83 | 9.22 | 96.67 | 98.36 | 7.78 |
| | Retaining member | 7.33 | 7.02 | | 13.39 | 10.33 | | 2.36 | 1.09 | |
| d | Filter | 80.18 | 71.21 | | 13.36 | 10.91 | | 0.67 | 0.53 | |
| | Tube | 13.44 | 18.79 | 8.75 | 73.46 | 77.64 | 9.95 | 98.20 | 98.98 | 10.16 |
| | Retaining member | 6.38 | 10.04 | | 13.19 | 11.56 | | 1.12 | 0.75 | |
| e | Filter | 78.89 | 75.96 | | 12.58 | 10.37 | | 0.75 | 0.63 | |
| | Tube | 14.00 | 16.22 | 8.32 | 73.68 | 79.55 | 8.75 | 97.98 | 98.31 | 8.55 |
| | Retaining member | 7.11 | 7.87 | | 13.74 | 10.21 | | 1.28 | 1.27 | |

*Indicates the percent contribution of the liquid in the total tube fluorescent intensity.

The present invention has been shown in the described embodiments for illustrative purposes only. The present invention may be subject to many modifications and changes without departing from the spirit or essential characteristics thereof. We therefore claim as our invention all such modifications as come within the spirit and scope of the following claims.

We claim:

1. An apparatus for use in collecting airborne particles comprising:

a collection vessel in which airborne particles are collected for analysis, the collection vessel comprising a microcentrifuge tube having an open end that is orthogonal to a line extending longitudinally with respect to the tube;

an air-inlet conduit for conducting air into the microcentrifuge tube, the air-inlet conduit extending at an angle with respect to a plane that is parallel to the open end, the air-inlet conduit being non-orthogonal and non-parallel to said plane; and an air-outlet conduit for conducting air out of the microcentrifuge tube;

wherein the air-inlet conduit and the air-outlet conduit are situated to cause air flowing through the microcentrifuge tube to create a vortex, thereby causing airborne particles to separate from the air flowing through the microcentrifuge tube.

2. The apparatus of claim 1 wherein:

the microcentrifuge tube is a first microcentrifuge tube, the air-inlet conduit comprises a first air-inlet conduit, and the air-outlet conduit comprises a first air-outlet conduit; and the apparatus further comprises:

a second microcentrifuge tube;

a second air-inlet conduit in fluid communication with the first air-outlet conduit so that air flowing through the first air-outlet conduit is conducted into the second microcentrifuge tube through the second air-inlet conduit, the second air-inlet conduit being non-orthogonal to a line extending longitudinally with respect to the second microcentrifuge tube; and a second air-outlet conduit for conducting air out of the second microcentrifuge tube;

wherein the second air-inlet conduit and the second air-outlet conduit are situated to cause air flowing through the second microcentrifuge tube to create a vortex, thereby causing airborne particles to separate from the air flowing through the second microcentrifuge tube.

3. The apparatus of claim 2, further comprising an air-flow member adapted to be removably coupled the first and second microcentrifuge tubes, wherein the first and second air-inlet conduits and the first and second air-outlet conduits are respective passageways defined in the air-flow member.

4. The apparatus of claim 2, wherein the first microcentrifuge tube is supported in the same orientation as the second microcentrifuge tube.

5. The apparatus of claim 1, further comprising a vacuum source fluidly connectable to the air-outlet conduit to draw air through the microcentrifuge tube.

6. The apparatus of claim 1, wherein:
the open end of the microcentrifuge tube is the only opening in the tube;
the air-inlet conduit conducts air to flow into the microcentrifuge tube through the open end; and
the air-outlet conduit conducts air to flow outwardly from the microcentrifuge tube through the open end.

7. The apparatus of claim 1, further comprising an air-flow member adapted to be removably coupled the microcentrifuge tube, wherein the air-inlet conduit comprises a first passageway defined in the air-flow member and the air-outlet conduit comprises a second passageway defined in the air-flow member.

8. The apparatus of claim 7, wherein the air-outlet conduit comprises an extension portion of the air-flow member that is in communication with the second passageway and extends into the microcentrifuge tube through the open end thereof.

9. The apparatus of claim 1, wherein the air flow in the collection vessel microcentrifuge tube is a reverse-flow cyclone.

10. The apparatus of claim 1 having a 50% cut-off diameter of 2 microns.

11. A method for collecting airborne particles for analysis, the method comprising:
flowing air through the open end of a microcentrifuge tube along a flow path in a direction that extends generally tangentially with respect to an inner surface of the microcentrifuge tube, the open end being orthogonal to a line extending longitudinally with respect to the tube, the flow path being non-orthogonal and non-parallel to a plane defined by the open end, wherein the air flowing through the microcentrifuge tube establishes a cyclone; and separating airborne particles from the air flowing through the microcentrifuge tube.

12. The method of claim 11, wherein the air flowing through the microcentrifuge tube establishes a reverse-flow cyclone.

13. The method of claim 11, wherein the air flowing into the microcentrifuge tube is conducted through an inlet conduit of an air-flow fitting coupled to the microcentrifuge tube, and wherein air flowing out of the microcentrifuge tube is conducted through an outlet conduit of the air-flow fitting.

14. The method of claim 11, wherein air flowing outwardly from the microcentrifuge tube is conducted into a secondary collection vessel to further separate airborne particles from the air flow.

15. The method of claim 11, further comprising performing an analysis of the particles separated from the air while the particles are still in the microcentrifuge tube.

16. The method of claim 15, wherein performing an analysis of the particles comprises performing PCR on the particles while the particles are still in the collection vessel.

17. The method of claim 15, wherein performing an analysis of the particles comprises detecting for the presence of a specific type of particle while the particles are still in the collection vessel.

18. The method of claim 17, wherein the presence of a specific type of particle is detected by an assay that is contained in the collection vessel as air flows through the collection vessel and particles are separated from the air.

19. An apparatus for use in collecting airborne particles comprising:

a collection vessel in which airborne particles are collected for analysis, the collection vessel comprising a microcentrifuge tube having an open end that is orthogonal to a line extending longitudinally with respect to the tube; and an air-flow member configured to be coupled to the microcentrifuge tube, the air-flow member comprising an air-inlet conduit adapted to direct air through the open end and into the microcentrifuge tube and an air-outlet conduit adapted to receive air flowing outwardly through the open end of the microcentrifuge tube, the air-inlet conduit extending at an angle with respect to a plane that is parallel to the open end, the air-inlet conduit being non-orthogonal and non-parallel to said plane, wherein the air-inlet conduit and the air-outlet conduit are situated to cause air flowing through the collection vessel to create a vortex, thereby causing airborne particles to separate from the air flowing through the collection vessel.

20. The apparatus of claim 19, wherein the open end of the microcentrifuge tube is the only opening in the microcentrifuge tube.

21. The apparatus of claim 19, further comprising a vacuum source fluidly connectable to the air-outlet conduit to draw air through the collection vessel.

22. The apparatus of claim 19 having a 50% cut-off diameter of 2 microns.

23. The apparatus of claim 19, wherein the microcentrifuge tube comprises a first microcentrifuge tube, the apparatus further comprises a second microcentrifuge tube having an open end, the air-inlet conduit comprises a first air-inlet conduit adapted to direct air through the open end of the first microcentrifuge tube and into the first microcentrifuge tube, the air-outlet conduit comprises a first air-outlet conduit adapted to receive air flowing outwardly through the open end of the first microcentrifuge tube, and the air-flow member further comprises an intermediate fluid conduit, a second air-inlet conduit adapted to direct air from the first microcentrifuge tube to flow into the second microcentrifuge tube via the open end thereof, and a second air-outlet conduit adapted to receive air flowing outwardly through the open end of the second microcentrifuge tube, the intermediate fluid conduit being in fluid communication with the first air-outlet conduit and the second air-inlet conduit such that air from the first microcentrifuge tube flows through first air-outlet conduit, the intermediate conduit, the second air-inlet conduit and into the second microcentrifuge tube, the second air-inlet conduit and the second air-outlet conduit being situated to cause air flowing through the second microcentrifuge tube to create a vortex, thereby causing airborne particles to separate from the air flowing through the second microcentrifuge tube.

24. The apparatus of claim 19, wherein the first microcentrifuge tube is supported side-by-side in the same orientation as the second microcentrifuge tube.

25. The apparatus of claim 19, wherein the air-flow member is configured to support both the first and second collection vessels in a generally vertically upright orientation during use.

26. The apparatus of claim 19, wherein the particles deposited in the first microcentrifuge tube are generally larger than the particles deposited in the second microcentrifuge tube.

27. The apparatus of claim 19, wherein the air-inlet conduit extends at an angle of about 30° to 45° with respect to the plane.

28. The apparatus of claim 19, wherein the air-outlet conduit is parallel to a longitudinal axis of the microcentrifuge tube.

29. The apparatus of claim 19, wherein the air-flow member is threaded to receive corresponding threads on the microcentrifuge tube so that the microcentrifuge tube can be easily screwed onto and removed from the air-flow member.

* * * * *